ically cured polymeric material is [sic]

United States Patent [19]
Jones

[11] Patent Number: 4,978,391
[45] Date of Patent: Dec. 18, 1990

[54] INTRAORAL MEDICAMENT DELIVERY AND PROCEDURE

[75] Inventor: Leslie A. Jones, York, Pa.

[73] Assignee: Dentsply Management Corp., York, Pa.

[21] Appl. No.: 331,074

[22] Filed: Mar. 27, 1989

Related U.S. Application Data

[63] Continuation of Ser. No. 120,280, Nov. 13, 1987, abandoned.

[51] Int. Cl.$^5$ .................. C09K 3/00; A61K 6/08; A61C 7/12
[52] U.S. Cl. .................. 106/35; 433/208; 433/8; 523/122
[58] Field of Search .............. 106/35; 433/208, 8; 523/122

[56] References Cited

U.S. PATENT DOCUMENTS

| | | | |
|---|---|---|---|
| 1,721,334 | 7/1929 | Dillman | 433/215 |
| 3,527,219 | 9/1970 | Greenberg | 433/215 |
| 3,600,807 | 8/1971 | Sipos | 433/229 |
| 3,618,213 | 11/1971 | Shephard et al. | 433/168.1 |
| 3,746,555 | 7/1973 | Muhler | 433/229 |
| 3,754,332 | 8/1973 | Warren, Jr. | 433/217.1 |
| 3,911,100 | 10/1975 | Sim et al. | 433/215 |
| 4,175,326 | 11/1979 | Goodson | 433/80 |
| 4,220,552 | 9/1980 | Hitchcock | 424/52 |
| 4,226,848 | 10/1980 | Nagai et al. | 424/434 |
| 4,286,592 | 9/1981 | Chandrasekaran | 424/448 |
| 4,292,299 | 9/1981 | Suzuki et al. | 424/433 |
| 4,362,842 | 12/1982 | Masuhara et al. | 524/854 |
| 4,435,160 | 3/1984 | Randklev | 523/118 |
| 4,496,322 | 1/1985 | Sandham et al. | 433/217 |
| 4,515,910 | 5/1985 | Rawls et al. | 523/115 |
| 4,523,910 | 6/1985 | Makovich | 433/215 |
| 4,533,326 | 8/1985 | Anthony | 433/229 |
| 4,554,154 | 11/1985 | White | 433/216 |
| 4,568,535 | 2/1986 | Loesche | 424/28 |
| 4,568,536 | 2/1986 | Kronenthal et al. | 424/22 |
| 4,676,752 | 6/1987 | Lefkowitz | 433/229 |
| 4,681,544 | 6/1987 | Anthony | 433/215 |
| 4,772,325 | 9/1988 | Kwan et al. | 106/35 |
| 4,778,834 | 10/1988 | Murray | 523/212 |
| 4,813,875 | 3/1989 | Hare | 523/109 |

FOREIGN PATENT DOCUMENTS

| | | |
|---|---|---|
| 753612 | 2/1967 | Canada . |
| 917075 | 12/1972 | Canada . |
| 936472 | 11/1973 | Canada . |
| 1085726 | 9/1980 | Canada . |
| 1125698 | 6/1982 | Canada . |
| 1175596 | 10/1984 | Canada . |
| 1196219 | 11/1985 | Canada . |
| 1197715 | 12/1985 | Canada . |
| 140766 | 10/1984 | European Pat. Off. . |
| 301516 | 7/1988 | European Pat. Off. . |
| 3610808 | 10/1986 | Fed. Rep. of Germany . |

Primary Examiner—A. Lionel Clingman
Assistant Examiner—James M. Silbermann
Attorney, Agent, or Firm—David E. Wheeler; Edward J. Hanson, Jr.; D. James Picciano

[57] ABSTRACT

A method for cushioning dental appliance in the mouth using a visible light cured polymeric material which can also be used in a method for intraoral medicament delivery in the mouth is provided. When used with an orthodontic bracket, for example, the light cured polymeric material is dispensed on the orthodontic bracket after the bracket is in place and the material is light cured on the bracket. When used in a method of intraoral delivery of a medicament, a medicament is added to the polymeric material and the polymeric material is applied in the same manner as described for cushioning an orthodontic bracket.

22 Claims, 1 Drawing Sheet

INTRAORAL MEDICAMENT DELIVERY AND PROCEDURE

This is a continuation of application Ser. No. 120,280, filed Nov. 13, 1987, now abandoned.

BACKGROUND OF THE INVENTION

This invention relates to means for protecting soft oral tissue from the irritating effects of dental devices and/or the provision of medicaments or therapeutics in measured doses within the oral cavity.

Devices for timed release of therapeutic drugs have been described in the prior art. For example, the National Institute for Dental Research has described a preformed kidney shaped polymer sac containing fluoride salt in a matrix of hydrophilic polymer that moderates and controls the diffusion of fluoride ion into the oral environment. These devices have been attached to a tooth by an adhesive. Their periodical replacement is time costly and their size makes them cumbersome. Despite these difficulties their use is contemplated to control rampant caries, for example.

Orthodontics is a discipline within dentistry that is concerned with the movement of teeth to achieve satisfactory occlusive interlation between teeth. In order to achieve this, metal or ceramic devices called brackets are attached to the teeth. The brackets can be adhered to each other by mechanical interlocks formed in the bracket and to the tooth by micromechanical interlocks formed by acid etching of the dental enamel prisms of hydroxy apatite. A layer of a self curing or actinic light cured resin or cement is applied between these interfaces and hardened to retain the bracket even when subjected to considerable force. Force is applied through bracket wire that travels between brackets attached to the several teeth and is placed under tension by mechanical forces induced by beding the wire. The relief of the induced tension occurs as the teeth move. The forces cause the breakdown of tissue on one side and the build-up of tissue on the other. Because there is excessive force required at the wire terminus or in molar teeth that have multiple roots, it is common that the bracket have a continuous band surrounding it in these situations. The bracket extends buccally and has a receptacle for the wire, and is sufficiently large to permit the transfer of the wire stress to the tooth. The protrusion of the bracket toward the cheek and lips (or tongue in specialized applications), and the sharp and distinct edges of the bracket, and the presence of wire ends are all irritating factors for the adjacent soft tissue and the patient. In due course the tissue may become calloused. Corrective methodology for this problem is for the patient to apply beeswax to the bracket where and when required, especially during the break-in period.

The presence of this bulky bracket makes cleaning of the teeth difficult. The tooth is no longer self-cleansing and it is difficult for the patient to clean the tooth mechanically. Plaque frequently builds-up around the apical walls of the bracket, causing conditions conducive to caries and at the gingival crest gingivitis, and possibly inducing more serious periodontal conditions. These and other abnormal conditions suggest the need to provide therapeutical substrates locally on a sustained basis.

In one preferred form the device consists of a light curing elastomeric material that may, depending on the application, contain a therapeutic agent that is released into the oral cavity through extraction by saliva.

SUMMARY OF THE INVENTION

A method for intraoral tissue released delivery of a medicament in the oral cavity is provided. The method comprises the steps of affixing a base to a tooth, applying a prepolymer containing a medicament to the base and polymerizing the prepolymer to affix the resulting polymeric material to the base. In preferred embodiments, the method further comprises selecting the prepolymer to have properties such that the medicament is extracted from the polymeric material by salvia in the oral cavity, e.q., the polymer is preferably hydrophilic in some applications. The method may further comprise the step of providing the base in the form of an orthodontic bracket which is used to straighten teeth. The method of the invention may be used to treat dental caries and/or periodontal disease, and the particular treatment selected will reflect the medicament or medicaments selected to be incorporated in the prepolymer.

Also, a method for cushioning a dental appliance in the oral cavity is provided. The method comprises the steps of affixing a dental appliance in the oral cavity, applying a prepolymer to the dental appliance and polymerizing the prepolymer to affix the resulting polymeric material to the base. In preferred embodiments, the method further comprises selecting the prepolymer to be hydrophilic so that it is lubricated naturally by saliva in the mouth, and so that it is soft and pliable so that it is comfortable in the mouth and can easily be removed using standard dental cutting tools.

An apparatus for intraoral time released delivery of a medicament in the oral cavity is also provided. The apparatus comprises a base adapted to be affixed to a tooth, and a polymeric material containing a medicament or medicaments affixed to the base. In the preferred embodiment the apparatus will further comprise a polymeric material having properties such that the medicament is extracted from the polymeric material by saliva in the oral cavity (e.g., a hydrophilic polymer). Also preferred is the apparatus wherein the base comprises an orthodontic bracket.

As used herein, base may represent a band or bracket or any similar device used in dentistry.

The method and apparatus of the invention provide a means and a method for a more permanent covering of brackets to reduce irritation of the soft tissue in the mouth and provide a comfortable and biocompatible covering, for example, during orthodontic treatment, as compared to using, for example, beeswax The polymer used in the invention has properties such that the coating can be easily, conveniently, and rapidly removed in the dentist's office, and may be conveniently and rapidly replaced without pretreatment of the bracket. The coating can be, and preferably will be adapted to contain a therapeutic substance that can be delivered to the oral cavity to treat any attendant oral condition. Accordingly, in orthodontic treatment for example, the orthodontist may conveniently use a prepolymer containing a fluoride to prevent cavities in teeth under the orthodontic bracket, and replace the coating monthly, for example, to assure that an effective quantity of fluoride is in the mouth, without having to remove and replace, or adjust the orthodontic brackets.

DETAILED DESCRIPTION OF THE INVENTION

Figure 1:
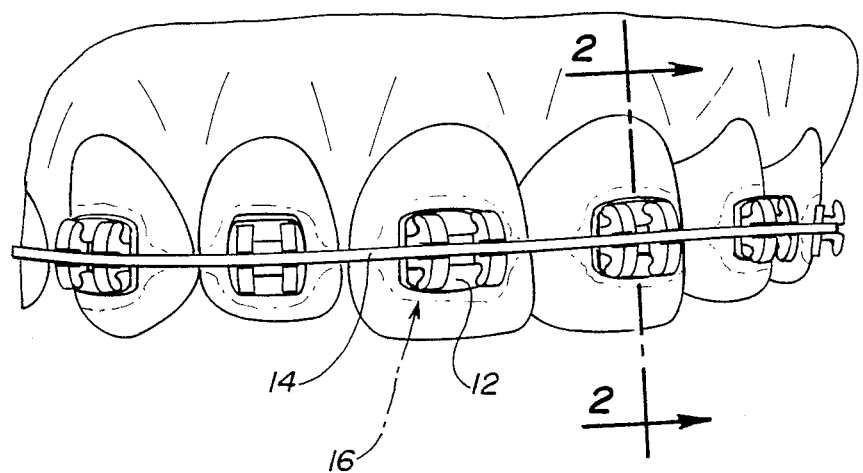
FIG. 1 illustrates a set of teeth having orthodonic brackets attached with a beding wire and a coating of polymeric material.
Figure 2:
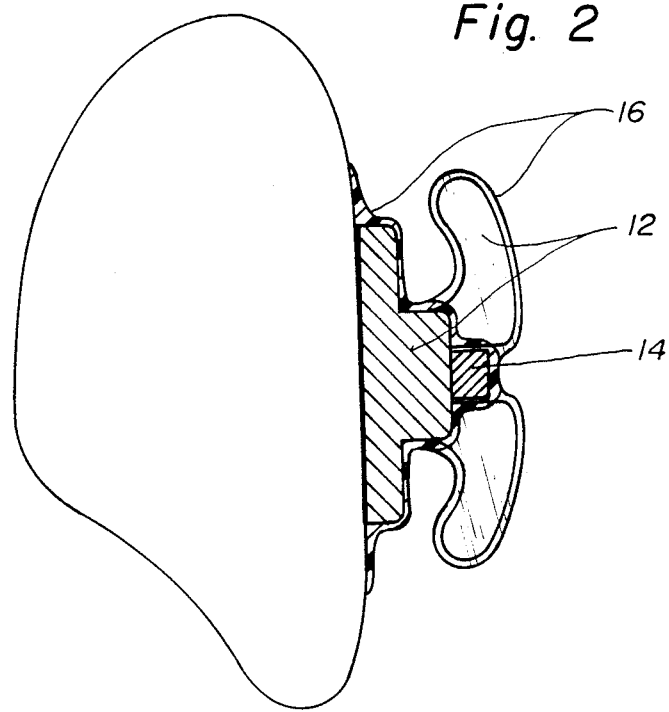
FIG. 2 illustrates a view through line 2—2 of FIG. 1.

With reference now to FIGS. 1 and 2, an illustrated base of the invention for holding polymeric material in the mouth is orthodonic bracket 12. Orthodonic bracket 12 is preferably made of a metal or other suitable material such as glass or ceramic, for example aluminates, silicates, titanates, zirconates and mixtures thereof and including sodium, potassium, titanium and other compositions thereof. The ceramic materials used may employ fiber and whisker reinforcements of the same materials; single crystal materials such as sapphire, zircon, and the like; spinels; and intermetallic compounds; glass ceramics or nitrides; borides or carbides; or chromium, cobalt, nickel, steels, for example, and alloys thereof.

The orthodontic bracket is attached to the tooth by first acid etching the enamel of the tooth, and optionally the bracket, to provide a surface which will interact with an appropriate adhesive formulated to attach metal, ceramic glasses and/or crystals to bone or teeth. After a suitable number of brackets 12 have been attached to a like number of teeth, the brackets are connected by a beding wire 14 which, when properly anchored, exerts a force on each of the brackets, which in turn exert a force on each of the teeth in a manner that has a tendancy to cause alignment of the teeth. A prepolymer of polymeric material 16 is then placed on the brackets and/or the beding wire, and is cured in situ.

Polymeric material 16 preferably is a relatively soft elastomeric polymer which holds the brackets 12 and wire 14 firmly, but does not, relatively speaking, irritate the soft tissue of the mouth that comes into contact with the orthodontic bracket. Polymeric material 16, when cured, is structurally a relatively permanent part of the orthodontic brackets 12 and wire 14, and is not easily dislodged and does not easily wear away like beeswax, which is commonly used in the art for the purpose of cushioning, i.e. reducing the irritating effects of dental appliances in the mouth by covering irregularities such as ends of wires and other protrusions. Although polymeric material 16 does not wear away, since it is relatively soft and pliable, it can be easily cut away from the brackets 12 using conventional dental tools.

Although illustrated as being a thin film over bracket 12 and wire 14, it will be recognized by those skilled in the art that polymeric material 16 may fill the interstices between the bracket and the tooth and the wire and the tooth.

The preferred prepolymer used herein is described in copending U.S. Ser. No. 944,476 filed Dec. 19, 1986, and in copending U.S. Ser. No. 120,269 filed Nov. 13, 1987 the disclosure of which is incorporated herein by reference.

Mixtures of the above referenced exemplary prepolymers and other similar oligomers may be used as the sole polymerizable ingredient; or the fluid polymerizable composition may include other diluent comonomers such as lower viscosity diluent monomers and oligomers, for example polyethylene glycol dimethacrylate, butylene glycol dimethacrylate and the like. All diluent monomers are characterized as having low volatility and toxicity.

Additional exemplary prepolymers for use in the present invention include: polysiloxanedimethacrylates, polyorganosilylenes—for example—polydimethyl-silylene-co-phenylmethylsilylene, polycarbonate urethane dimethacrylates, ethoxylated bisphenol A dimethacrylate, 2,2-Bis[4-(3-methacryloxy-2-hydroxypropoxy)-phenyl]propane (BISGMA), and 2,2-Bis [4-(2-methacryloxy-2-methylethoxy)phenyl]propane (BISIPMA).

The prepolymer of polymeric material 16 will preferably contain a medicament for time released delivery thereof. In the application where the base is to be used in the mouth, the mechanism of the release of the medicament will be extraction by saliva. Accordingly, in such an application, the polymer will be chosen so that it has properties which will facilitate this extraction and will be, for example, hydrophilic.

When used in the mouth, the medicaments added to the prepolymer will be selected from medicaments such as those known to treat or prevent dental caries or periodontal disease. Illustrative of such medicaments are sodium fluoride and chlorohexidine for the treatment or prevention of dental caries, and hypochlorite for the treatment of periodontal disease.

Another important embodiment of the present invention provides treatment membranes which serve as a repository and long term dispenser of a wide range of therapeutic agents useful in treating mammals. These therapeutic agents may be incorporated into the treatment membrane of the present invention by mixing or encapsulation.

Examples of therapeutic agents include those for treating infection by such organisms as Streptococcus mutans (which is causally implicated in dental caries), or A. actinomycetemcomitans and β gingivalis (which are causally linked with periodontal disease), or the like. Exemplary of these therapeutic agents are the following examples arranged by structure and clinical use:

1. Antiseptics and Germicides
    a. ethanol and isopropanol
    b. iodine preparations
        (1) iodine, U.S.P.
        (2) Providine-Iodine
        (3) iodoform
        (4) thymol iodine
    c. thimerosal (Merthiolate)
    d oxidizing agents
        (1) urea peroxide
        (2) chlorine dioxide
        (3) benzoyl peroxide
    e. Phenolic Compounds
        (1) eugenol, U.S.P.
        (2) Guaiacol (2-Methoxyphenol)
    f. Quaternary Ammonium Compounds
        (1) Benzalkonium Chloride. U.S.P.
        (2) Benzethonium Chloride (Phemerol Chloride)
2. Non-antibiotic Antimicrobials
    a. Chlorhexidine
    b. Silver Nitrate (1%)
    c. silver sulfadiazine (1%)
3. Antibiotics
    a. Penicillins
    b. Tetracyclines
    c. Erythromycins
    d. Cephalosporins
    e. NBH (1% neomycin, 1% bacitracin. 0.5% hydrocortisone)

f. metnanidasole
4. Antifungal agents
 a. triacetin
 b. ciclopirox olamine
 c. clotrimazole
 d. griseofulvin
 e. miconazole nitrate (2%)
 f. Castellani Paint (basic Fuchsin, Phenol, Resorcinol, acetone, alcohol.
 g. amphotericin B
 h. Nystatin
5. Steroidal Antiinflammatory agents
 a. Triamcinolone acetonide (0.1 to 1% by weight)
 b. Cortisol acetate (0.01 to 1% by weight)
6. Non-steroidal antiinflammatory agents
 a. salicylates
 b. indomethacin
 c. ibuprofen
 d. fluoribuprofen
 e. 2-[3-(1,1-dimethyl)-5-methoxyphenyl]oxazolo[4.5b]pyridine
7. Antiviral agents
 a. triamcinolone
8. Non-fluoride tooth desensitizing agents
 a. strontium chloride 10%
 b. sodium citrate 1.5%
 c. Potassium Nitrate 5%
9. Wound healing agents and anti-collagenase (protease) agents
 a. fibronectin (plasma)
 b. tripeptides
 c. short chain peptides up to 20 amino acids in length which exhibit wound healing or anticollagenase (antiprotease) or antielastase activity.
10. Topical anaesthetics
 a. Benzocaine, U.S.P. (ethyl 4-aminobenzoate) (0.1 to 20% by weight)
 b. Chlorobutanol, N.F., (1,1,1-Trichloro-2-methyl-2-propanol), (0.01 to 10% by weight).
 c. Lidocaine, U.S.P, (Alpha-diethylamino-2, 6-acetoxyiodide hydrochloride), (0.01 to 10% by weight).
 d. Butacaine Sulfate, U.S.P., (3-dibutyl aminopropyl 4-aminobenzoate sulfate), (0.1 to 4% by weight).
 e. Tetracaine Hydrochloride, U.S.P., (2-dimethyl aminoethyl 4-butylaminobenzoate hydrochloride), (0.1 to 2% by weight).
 f. Dyclonine Hydrochloride U.S.P., (4-butoxy-3-piperidino propriophenone hydrochloride), (0.05 to 1% by weight).

Although it will be recognized by those skilled in the art that polymer 16 can be cured using any curing system known in the art, in the preferred embodiment the prepolymer will be formulated to be cured by actinic light in the visible wavelength range. Preferably, the prepolymer will be cured using light in the range of 380–600 nm, and more preferably in the range of about 450–520 nm.

In a method of the invention for intraoral delivery of a drug, the practitioner, for example an orthodontist, will first attach the base, for example an orthodontic bracket, to a tooth by any suitable means. For example, the enamel of the tooth may be etched using acid etching techniques well known in the art, and an adhesive that provides a suitable bond to both the base and the etched tooth may be applied to the tooth, the base, or both and upon hardening the base will be adhered to the tooth. The practitioner can then apply a quantity of prepolymer, having the medicament of choice, or a mixture of medicaments included therein, to the (bracket) base attachment and/or wires. The prepolymer can then be affixed to the base (brackets) by polymerization of the prepolymer. In the preferred embodiment of the invention, this will be done by irradiating the prepolymer with a curing device known as a Prismetics ® light equipped to deliver visible light radiation. The Prismetics ® light is a product of the L. D. Caulk Division of Dentsply International Inc.

The medicament included in the prepolymer will be extracted by the saliva for a period of time from the polymeric material to the oral cavity. When the concentration of medicament in the polymer reaches a low level, after about a month or at a convenient patient recall visit, the practitioner can remove the elastomeric polymer from the base (brackets) using a cutting instrument, and a fresh layer of replacement polymer can be added to the base (bracket) without further treatment of the base. Retention of the polymer on the base is preferably primarily due to a mechanical interlocking of the in situ formed polymeric material with the base. Those skilled in the art will recognize that the base may be etched and treated with a chemical, e.g. a silane, to provide a chemically compatible surface for adhesive bonding of the polymer to the base.

In a second method of the invention, for cushioning a dental appliance in the mouth, the practitioner will first attach a dental appliance, for example an orthodontic bracket, in the mouth, and will then apply a quantity of prepolymer to the appliance, and will then polymerize the prepolymer preferably using light in the visible wavelength range.

Preferred prepolymers described herein are particularly suitable for the method of cushioning a dental appliance because they are hydrophilic, i.e. wettable, so that saliva in the mouth wets the polymer and maintains its wetness so the polymer is lubricated so that epitheial tissue in the mouth readily slide over the polymer. When soft materials in the mouth are dry, they tend to be uncomfortable because epithelial tissue stick to them. The prepolymer will preferably be chosen so that the polymer formed therefrom is elastomeric and is relatively soft and pliable. These properties contribute significantly to the comfort of the polymer in the mouth. Because the polymer is tough and elastomeric, the polymeric protective cushion is long lasting and has good integrity.

Examples of compositions of the prepolymer which can be used with the present invention are illustrated as follows:

EXAMPLE 1

Resin 1 Preparation

An isocyanatoethyl methacrylate urethane methacrylate oligomer elastomer prepolymer compound was prepared according to the following formulation

| | |
|---|---|
| Polypropylene glycol (MW 4000) Voranol 2140 (Dow Chemical) | 834.6 g |
| Trimethylhexamethylene diisocyanate (Thorson Chemicals) | 87.7 g |
| Stannous octoate | 0.50 g |
| Hydroxyethyl methacrylate (Rohm & Haas) | 27.1 g |
| 1,4 Butanediol (BASF) | 18.7 g |
| Isocyanatoethyl methacrylate | 30.8 g |

The procedure was as follows:

In theory, one mole of polypropylene glycol (2 equivalents of hydroxy) are reacted with two moles of trimethylhexamethylene diisocyanate (4 equivalents of isocyanate) employing the stannous octoate as catalyst The polypropylene glycol was charged into a 2 liter reacter. Stirring and dry air flow through the reactor was begun. The stannous octoate was charged to the reactor and stirred. The trimethylhexamethylene diisocyanate was then added to the glycol catalyst mixture dropwise using a separatory funnel. The addition was done at room temperature and was controlled to keep the temperature below 50° C. Addition was complete after 30 minutes. The contents were allowed to stir for 30 minutes more. Samples were taken and titration was done to determine isocyanate content. Isocyanate was found to be 1.9% which indicated complete reaction of the polypropylene glycol and trimethyhexamethylene diisocyanate. Then the 27.1 grams of hydroxyethy methacrylate HEMA were added all at once to the reactor contents which were at a temperature of about 40° C. The contents were allowed to stir for 45 minutes, then titration samples were taken and the isocyanate content determined to be 0.95%. This indicated complete reaction of the HEMA with the isocyanate terminated prepolymer leaving 1 equivalent of isocyanate sites for reaction with 1,4 butane diol. At this point 18.7 grams of 1,4 butane diol were added to the reactor contents all at once and allowed to stir in for 2 hours. The temperature of the reactor continued between 40° and 50° C. for this procedure. At the end of 2 hours the isocyanatoethyl methacrylate was added dropwise to the reactor using a separatory funnel. This addition took approximately 30 minutes. Stirring was continuous until the next morning to be sure all the free isocyanate was reacted. Then the pot contents were unloaded.

Coating Preparation

A visible light curable coating of the following formulation was compounded by a double planetary mixer at reduced pressure. The ingredients were added in the order listed in the absence of visible light.

| Resin of EXAMPLE 1 | 373.5 g |
| --- | --- |
| Camphorquinone | 0.76 g |
| 4-Dimethylaminobenzonitrile | 3.49 g |
| Butylated Hydroxy Toluene | 0.163 g |
| Titanium IV neoalkoxy, tris (dodecylbenzene) sulfanato (Ken React LICA 09 from Kenrich Petrochemicals, Inc.) | 0.30 g |
| Silanated/ground Quartz (mean particle size of 10-15 microns) | 464.8 g |
| fumed silica (Aerosil R-972 from Degussa) | 155.0 g |
| Rocket red fluorescent pigment (Dayglo) | 0.214 g |

The composition was irradiated for 10 seconds using Prismetics ® light. A sample of material 20 mm thick was covered with a sheet of clear Mylar about 1 mil thick. The sheet was in direct contact with the sample. The light was directly engaged against the sheet of Mylar. The material cured to a rubbery solid to a depth of 13 mm. The uncured composition was removed by wiping.

Water sorption and solubility measurements were taken on the cured material with the results given below:

| * 1 Week Water Sorption (mg/cm$^2$) | 0.61 |
| --- | --- |
| ** 1 Week Water Solubility (%) | 0.20 |

The composition is non-tacky in use after polymerizing to set using a Prismetics ® light.

EXAMPLE 2

Resin 2 Preparation

A urethane dimethacrylate was prepared according to the following formulation:
Hydroxy propyl methacrylate (HPMA): 59.18%
Trimethylhexamethylene diisocyanate (TMDI): 40.75%
Stannous octoate: 0.05%
Methyl ether hydroquinone: 0.02%

Procedure: The hydroxy propyl methacrylate stannous octoate, and methyl ether hydroquinone were weighed into a dry two liter reactor. Stirring and dry air flow through the reactor were begun. The reactor contents were heated to 50° C. and were continually stirred for 30 minutes to form a homogenous solution. The TMDI was weighed into a beaker and poured into a 250 ml addition funnel where it was next added dropwise to the reactor. The drop rate was monitored to keep the temperature between 50°-60° C. The next morning, a sample was taken and found to be free of residual diisocyanate. Then the reactor contents were unloaded.

Resin 3 Preparation

A polyether urethane dimethacrylate was prepared according to the following formulation:
Pluracol 628(polypropylene glycol nw 4,000): 93.61%
Isocyanatoethyl methacrylate (IEM): 6.34%
Stannous octoate: 0.05%

Procedure: The Pluracol 628 and stannous octoate were weighed into a dry two liter reactor. Stirring and dry air flow through the reactor were begun. The IEM was weighed into a beaker and poured into a 250 ml addition funnel where it was added dropwise to the reactor. The addition of IEM was done keeping the temperature below 50° C. Addition took 30 minutes. After addition the contents were allowed to stir 36 hours at a temperature between 40°-50° C.; then a sample was taken, found to be free of residual isocyanate, and the reactor contents unloaded.

Coating Preparation

A visible light curable coating of the following formulation was compounded by a double planetary mixer at reduced pressure:

| *Resin mixture (Resin 2 - 20 parts and Resin 3 - 80 parts) | 241.3 g |
| --- | --- |
| Camphorquinone | 0.5 g |
| 4-Dimethylaminobenzonitrile | 2.2 g |
| Butylated Hydroxy toluene | 0.244 g |
| Silanated Ground Quartz (Mean particle size of 10-15 microns) | 565.1 g |
| fumed silica (Aerosil R-972) | 188.1 g |
| Neoalkoxy, tridodecylbenzene-sulfonyl titanate (Ken React LICA 09) | 2.5 g |
| Rocket Red Fluorescent Pigment (Dayglo) | 0.260 g |

*Resin 2 and Resin 3 were combined first and stirred for 30 minutes in a double planetary mill.

The composition was irradiated for 1 minute using the procedure of Example 1. The material cured to a flexible solid that was substantially stiffer than the solid produced in Example 1.

EXAMPLES 3-5

A series of coating samples were prepared based upon the composition of Example 1.

Varying amounts of sodium fluoride powder sieved to less than 250 microns was added to the coating composition of Example 1 to produce compositions 3, 4, and 5. These were made into discs having a diameter of 20 mm and a thickness of 1 mm by filling a Mylar backed stainless steel ring, inserting a small piece of nylon string, smoothing the surface, and curing for 1 minute on the top side only with a GE Photoflood lamp (EBV-NO.2). The top surface of the discs were left uncovered. The weight of each specimen was then recorded to the nearest 0.1 mg. The discs were prepared in 3 replications and extracted individually in deionized water by suspension in 11 ml of the water. Each day the micrograms of fluoride extracted were measured using an ion fluoride sensitive ion electrode in conjunction with a Fisher Accumet pH meter (model 825 mp). After the daily measurement was taken, the old water was discarded and fresh water was added to the specimens so that the daily extraction data was accurate. On weekends the data was collected for the three days. Original concentrations of sodium fluoride and extraction data are presented as such in Table 1 below:

TABLE 1

| Ex. | % NaF | \multicolumn{11}{c}{Micrograms Released Time (Days)} |
|---|---|---|---|---|---|---|---|---|---|---|---|---|---|
|  |  | 1 | 2 | 3 | 4 | 5-7 | 8 | 9 | 10 | 11 | 12-14 | 15 | 16 |
| 3 | 1% | 30.7 | 18.1 | 16.1 | 15.7 | 37.3 | 11.0 | 9.5 | 8.5 | 8.1 | 19.6 | 5.2 | 11. |
| 4 | 2% | 78.7 | 41.3 | 32.7 | 29.9 | 71.0 | 20.2 | 17.9 | 16.1 | 15.9 | 39.0 | 11.8 | 25. |
| 5 | 5% | 193.1 | 100.0 | 79.4 | 65.9 | 132.7 | 44.0 | 39.6 | 34.7 | 34.0 | 95.9 | 31.5 | 82. |

The discs were elastomeric when manipulated by hand.

EXAMPLES 6-8

A series of treatment membrane samples were prepared based upon the composition of Example 2, except that sodium fluoride (−250 um) was added. The original concentrations and extraction data (see examples 3-5 for testing procedure) are given in Table 2.

TABLE 2

| Ex. | % NaF | \multicolumn{11}{c}{Micrograms Released Time (Days)} |
|---|---|---|---|---|---|---|---|---|---|---|---|---|---|
|  |  | 1 | 2 | 3 | 4 | 5-7 | 8 | 9 | 10 | 11 | 12-14 | 15 | 16 |
| 6 | 1% | 80.8 | 51.8 | 46.6 | 38.9 | 90.5 | 18.0 | 11.0 | 6.7 | 4.6 | 6.0 | 1.1 | 1. |
| 7 | 2% | 132.4 | 83.6 | 73.3 | 66.3 | 157.9 | 32.5 | 21.4 | 13.5 | 7.9 | 9.7 | 1.41 | 2. |
| 8 | 5% | 287.3 | 175.7 | 137.6 | 122.4 | 324.3 | 97.4 | 85.7 | 74.2 | 61.2 | 121.2 | 25.3 | 28. |

The discs were elastomeric when manipulated by hand.

EXAMPLE 9

Voranol 2120 (polypropylene glycol) (MW 2000): 68.25%
TMDI (Trimethylhexamethylene diisocyanate): 14.34%
Stannous Octoate: 0.05%
HEMA (Hydroxyethyl methacrylate): 3.14%
1,4-Butanediol: 4.29%
TIM (Reaction product of TMDI and HEMA): 8.10%
HEMA: 1.82%
Phosphoric Acid - Water Solution (1:1): 0.0021%

The polypropylene glycol (Voranol 2120) with an average molecular weight of 2000 is first mixed with the phosphoric acid solution. This neutralizes residual base in the polypropylene glycol which can act as a catalyst in the prepolymer reaction with TMDI. Then the stannous octoate is added as the catalyst for urethane formation. A 2/1 excess of TMDI is added to form an isocyanate terminated prepolymer. Then part of the residual isocyanate is capped with HEMA. The remainder is chain extended with 1,4-Butanediol. Then TIM is added. TIM is the reaction product of 1 mole (2 equivalents) of TMDI and 1 mole (1 equivalent) of HEMA. It has one free isocyanate end and one methacrylate end when the reaction is complete. The isocyanate portion reacts with the remaining hydroxyl group from 1,4-Butanediol. Finally, a small amount of HEMA is added to react any residual isocyanate.

A comparison of moles and equivalents of the ingredients is seen below:

|  | Moles | Equivalents |
|---|---|---|
| Voranol 2120 | 1 | 2 |
| TMDI | 2 | 4 |
| HEMA | 0.7 | 0.7 |
| 1,4-Butanediol | 1.4 | 2.8 |
| TIM | 0.7 | 0.7 |
| HEMA | 0.4 | 0.4 |

Activated Resin

Resin described above: 98.78%
Camphorquinone: 0.20%
4-Dimethylaminobenzonitrile: 0.92%
Butylated Hydroxy Toluene (BHT): 0.10%

Syringeable Material

Activated resin described previously: 54.76%
Fused Quartz (average particle size 15-25 microns): 39.68%
Aerosil R-972 fumed silica: 1.55%
Dayglo A-19 Horizon Blue pigment: 0.25%
Palatinol 711P (Di-$C_{7-9-11}$) Alkyl Phtalate: 3.10%
Ken React LICA 09: 0.13%
Gamma-Methacryloxpropyltrimethoxysilane: 0.52%

The attached table provides a comparison of the properties of the material of this example as compared with ADA specs.

The material with either resin has the advantages of unlimited work time, no mixing, command cure, and a fast cure.

EXAMPLE 10

A gypsum model of a patients mouth was obtained and a baseplate was fashioned over it in gypsum. Extracted teeth were placed in appropriate positions so that in-vitro application of brackets and archwires could be made. Brackets were attached by acid etching and wires were attached mechanically by conventional means. A quantity of the drug delivery material sufficient to cover the metal was applied to each bracket attachment and wires. The drug delivery material was syringed onto a non-stick pad and shaped to a thickness of about 0.3 mm to about 5 mm using a teflon dental instrument. The mass of material was picked up using the teflon dental instrument and placed on the bracket area adjacent to the tooth surface making sure that the tooth surface was in contact with the material. It was affixed thereto by polymerization resulting from irradiation with a Prismetics ® light delivering visible light radiation. The material was cured using a curing cycle of about 10 seconds per tooth. Since a three tooth bracket was used, total curing time was about 30 seconds. It was demonstrated that the product could be removed easily using a hand cutting instrument. The material was removed from the bracket in a single piece without excessive force. The coating was replaced without pretreatment of the bracket in the same manner as before. Retention was based on the mechanical interlocking of the in-situ formed polymer.

While present embodiments of the invention and methods of practicing the same have been illustrated and described, it will be recognized by those skilled in the art that this invention may be otherwise variously embodied and practiced within the scope of the following claims.

What is claimed is:

1. A method for providing intraoral time released delivery of a medicament in the oral cavity comprising the steps of sequentially:
   (a) affixing a base to a tooth by applying a dental adhesive to a tooth and/or said base and then touching said base to said tooth,
   (b) applying a nontoxic prepolymer of a polyether, polyester, polyurethane, or mixtures thereof containing a medicament to said base said prepolymer comprising a compound of the general formula $R_1 \pm A \pm R_1$ wherein

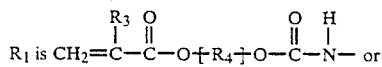
   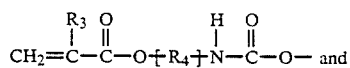

wherein $R_1$ may be the same or different $R_3$ is H, alkyl of 2-10 carbons, sub alkyl of 2-10 carbons, aryl of 6-14 carbon, sub aryl of 6-14 carbons, F, Cn and $R_3$ may be the same or different in each position;

$R_4$ is a divalent hydrocarbon radical or divalent sub hydrocarbon radical and may be straight or branched chain or acyclic or a combination thereof from 2-10 carbons; and is a polyurethane, polyether or polyester backbone; polysiloxanedimethacrylate, and polyorganosilylene, and (c) polymerizing to affix the resulting polymeric material to said base and to produce a polymer which is elastomeric, soft and pliable.

2. The method of claim 1 which further comprises the step of selecting said prepolymer to have properties such that said medicament is extracted from said polymeric material by saliva in the oral cavity.

3. The method of claim 1 which comprises the step of providing said base in the form of an orthodontic bracket which is used to straighten teeth.

4. The method of claim 1 which comprises the step of choosing said medicament for the purpose of treating dental.

5. The method of claim 4 which comprises the step of selecting said medicament from the group comprising antiseptics, germicides, antimicrobials, antibiotics, topical anaesthetics, antifungal agents, anti-inflammatory agents, antiviral agents, tooth desensitizing agents, wound healing agents and anti-collagenase agents.

6. The method of claim 1 which comprises the step of adding light activated initiators and accelerators to said prepolymer and adapting said prepolymer to be polymerized using light in the visible wavelength range.

7. The method of claim 6 which comprises the step of selecting said initiator to be camphorquinone.

8. The method of claim 1 comprising the step of affixing said base to said tooth after acid etching said tooth.

9. A method for cushioning dental appliance in the oral cavity comprising the steps of sequentially:
   (a) affixing a dental appliance in the mouth by applying a dental adhesive to a tooth and/or said dental appliance and then touching said dental appliance to said tooth,
   (b) applying a nontoxic prepolymer of a polyether, polyester, polyurethane, or mixture thereof to said dental appliance said polymer comprising $R_1 \pm A \pm R_1$ wherein

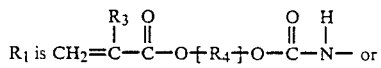
   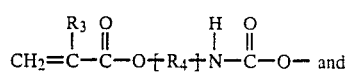

wherein $R_1$ may be the same or different $R_3$ is H, alkyl of 2-10 carbons, sub alkyl of 2-10 carbons, aryl of 6-14 carbon, sub aryl of 6-14 carbons F, CN and $R_3$ may be the same or different in each position;

$R_4$ is a divalent hydrocarbon radical or divalent sub hydrocarbon radical and may be straight or branched chain or acyclic or a combination thereof from 2-10 carbons; and is a polyurethane, polyether or polyester backbone; polysiloxanedimethacrylate, and polyorganosilylene, and (c) polymerizing said prepolymer to produce an elastic polymer which is soft and pliable using light in the visible wavelength range to affix the resulting polymeric material to said base.

10. The method of claim 9 which comprises the step of using a prepolymer which produces a polymer having hydrophilic properties.

11. The method of claim 9 which comprises the step of including a medicament in said prepolymer for slow release into the oral cavity.

12. An apparatus for intraoral time released delivery of a medicament in the oral cavity comprising:
  (a) a base comprising an orthodontic bracket adapted to be affixed to a tooth by adhering said base to said tooth using dental adhesive, and
  (b) a nontoxic polymeric material comprising polyether, polyester, polyurethane, or mixtures thereof containing a medicament affixed to said base, said polymer being elastic, soft and pliable said polymer comprising a crosslinked prepolymer comprising

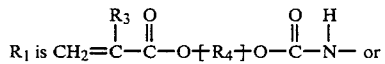

$R_1$ is

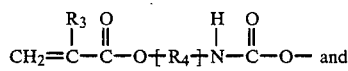

wherein $R_1$ may be the same or different $R_3$ is H, alkyl of 2-10 carbons, sub alkyl of 2-10 carbons, aryl of 6-14 carbon, subaryl of 6-14 carbons, F, CN and $R_3$ may be the same or different in each position;

$R_4$ is a divalent hydrocarbon radical or divalent sub hydrocarbon radical and may be straight or branched chain or acyclic or a combination thereof from 2-10 carbons; and is a polyurethane, polyether or polyester backbone; polysiloxanedimethacrylate, and polyorganosilylene.

13. The apparatus according to claim 12 in which said polymeric material has properties such that said medicament is extracted from said polymeric material by saliva in the oral cavity.

14. The apparatus according to claim 12 in which said medicament is adapted to treat dental disease and is selected from the group comprising antiseptics, germicides, antimicrobials, antibiotics, antifungal agents, anti-inflammatory agents, antiviral agents, tooth desensitizing agents, wound healing agents and anti-collagenase agents.

15. The apparatus according to claim 12 in which said polymeric material is a light cured polymeric material.

16. A method of cushioning a dental appliance in the oral cavity and producing intraoral time released delivery of a medicament to the oral cavity comprising the steps of sequentially:
  (a) affixing a dental appliance comprising orthodontic brackets to a plurality of teeth by applying a dental adhesive to said brackets and/or said teeth and then touching said brackets to said teeth,
  (b) applying a prepolymer of a polyether, polyester, polyurethane or a mixture thereof containing a medicament to said dental appliance said prepolymer comprising

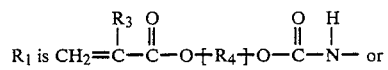

$R_1$ is

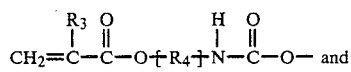

wherein $R_1$ may be the same or different $R_3$ is H, alkyl of 2-10 carbons, sub alkyl of 2-10 carbons, aryl of 6-14 carbon, sub aryl of 6-14 carbons, F, CN and $R_3$ may be the same or different in each position;

$R_4$ is a divalent hydrocarbon radical or divalent sub hydrocarbon radical and may be straight or branched chain or acrylic or a combination thereof from 2-10 carbons; and is a polyurethane, polyether or polyester backbone; polysiloxanedimethacrylate, and polyorganosilylene, and (c) polyumerizing said prepolymer to form an elastic, soft, pliable polymer and to at least mechanically attach the resulting polymeric material to said dental appliance.

17. The method of claim 16 which further comprises the step of selecting said prepolymer to have properties such that said medicament is extracted from said polymeric material by saliva in the oral cavity.

18. The method of claim 16 which comprises the step of providing said base in the form of an orthodontic bracket which is used to straighten teeth.

19. The method of claim !6 which comprises the step of choosing said medicament for the purpose of treating dental disease.

20. The method of claim 19 which comprises using a medicament which is a source of fluoride ions.

21. The method of claim 1 wherein said prepolymer is selected from the group consisting of -polydimethylsilylene-co-phenylmethylsilylene, polycarbonate urethane dimethacrylates, ethoxylated bisphenol A dimethacrylate, 2,2-Bis-propane (BISGMA), and 2,2-Bis-propane (BISIPMA).

22. A method for providing intraoral time released delivery of a medicament in the oral cavity comprising the steps of sequentially:
  (a) affixing a base to a tooth by applying a dental adhesive to a tooth and/or said base and then touching said base to a tooth
  (b) applying a non-toxic prepolymer of a polyether, polyester, polyurethane, or mixtures thereof containing a medicament to said base, and
  (c) polymerizing the prepolymer to affix the resulting polymeric material to said base and to produce an elastomeric polymer.

* * * * *